United States Patent [19]

Piccoli et al.

[11] Patent Number: 5,654,476

[45] Date of Patent: Aug. 5, 1997

[54] PROCESS FOR THE PREPARATION OF GEMFIBROZIL

[75] Inventors: Gianfranco Piccoli; Antonio Tarquini; Giovanni Frare, all of Milan, Italy

[73] Assignee: Recordati S.A. Chimical and Pharmaceutical Company, Chiasso, Switzerland

[21] Appl. No.: 553,329

[22] PCT Filed: May 10, 1994

[86] PCT No.: PCT/EP94/01508

§ 371 Date: Nov. 16, 1995

§ 102(e) Date: Nov. 16, 1995

[87] PCT Pub. No.: WO94/27948

PCT Pub. Date: Dec. 8, 1994

[30] Foreign Application Priority Data

May 20, 1993 [IT] Italy ................... MI93A1033

[51] Int. Cl.$^6$ .................................. C07C 59/68
[52] U.S. Cl. .................................. 562/471
[58] Field of Search ......................... 562/471

[56] References Cited

U.S. PATENT DOCUMENTS

| | | | |
|---|---|---|---|
| 2,516,611 | 7/1950 | Berhenke et al. | 260/521 |
| 4,126,637 | 11/1978 | Goel et al. | 562/421 |
| 4,254,262 | 3/1981 | Koike et al. | 546/287 |
| 4,665,226 | 5/1987 | Kearney | 562/471 |
| 4,734,511 | 3/1988 | Inagaki et al. | 549/273 |
| 5,041,640 | 8/1991 | Creger | 562/471 |

FOREIGN PATENT DOCUMENTS 0 575 303  12/1993  European Pat. Off. .
29 42 989  5/1980  Germany .

*Primary Examiner*—Gary Geist
*Assistant Examiner*—Barbara S. Frazier
*Attorney, Agent, or Firm*—Griffin, Butler, Whisenhunt & Kurtossy

[57] ABSTRACT

A process for the preparation of 2,2-dimethyl-5-(2,5-xylyloxy)-valeric acid, which process comprises the reaction of 2,5-dimethylphenol with a compound of formula (II),

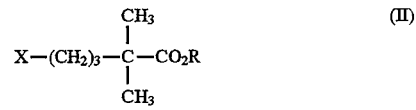

wherein R is an alkyl, aryl, arylalkyl group and —X is a halogen atom, and the subsequent hydrolysis to compound (I), characterized in that the reaction of compound (II) with 2,5-dimethylphenol is carried out in the absence of solvents and in the presence of an ammonium or quaternary phosphonium salt.

4 Claims, No Drawings

PROCESS FOR THE PREPARATION OF GEMFIBROZIL

This application is a 371 of PCT/EP94/01508, filed May 10, 1994.

BACKGROUND OF THE INVENTION

The present invention relates to a process for the preparation of gemfibrozil.

Gemfibrozil, or 2,2-dimethyl-5-(2,5-xylyloxy)-valeric acid, of formula (I):

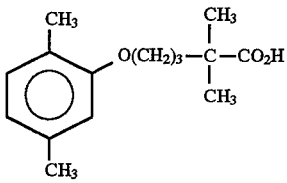

is a known hypolipemizing medicament widely used.

In USA, the market value of gemfibrozil in 1992 was estimated to be about 550 million dollars (SCRIP n. 1792, 5-2-93, p 7).

Therefore, it is evident the importance of methods allowing to prepare gemfibrozil in a cost-saving and industrially convenient way.

The up to now known methods do not solve satisfactorily the problem.

U.S. Pat. No. 3,674,836 discloses the reaction of a 3-(2,5-xylyloxy)propyl halide with an isobutyric acid 2-lithium derivative, to give compound (I). However, the use of lithium derivatives and anhydrous solvents involves evident drawbacks.

EP-219117 and JP-63 190 883 (Nitto Chemicals) disclose the preparation of ∝,∝-dimethyl-5-valerolactone by radicalic addition of HBr to 2,2-dimethyl-4-pentenoic acid and subsequent cyclization to lactone in alkali medium. The resulting compound was used by the Applicant as an intermediate for the preparation of gemfibrozil.

Finally, U.S. Pat. No. 4,665,226 envisages the reaction of 2,5-dimethylphenol with an 5-bromo- or 5-chloro-2,2-dimetilpentanoic acid ester, in a mixed solvent system (generally toluene/dimethylsulfoxide) under reflux for a time ranging from 7 to 20 hours.

The use of high-boiling solvents, which are difficult to remove, the high temperatures and the long reaction times make such a process scarcely attracting from the industrial point of view.

SUMMARY OF THE INVENTION

Now it has been found that the reaction of 2,5-dimethylphenol with a 5-bromo- or 5-chloro-2,2-dimetilpentanoic acid ester of formula (II):

wherein R is an alkyl, aryl, arylalkyl group and X is a halogen atom, can advantageously be carried out in the absence of solvents and in the presence of an ammonium or phosphonium quaternary salt.

DESCRIPTION OF PREFERRED EMBODIMENTS

In compounds (II), X is preferably chlorine or bromine, more preferably bromine, whereas R is preferably $C_1$-$C_6$ alkyl, more preferably methyl or ethyl.

As an ammonium or phosphonium quaternary salt, tetrabutylammonium bromide is preferred.

The intermediate of formula IIa is particularly preferred

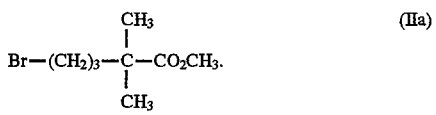

Compounds (II) can be prepared with known, conventional methods, for example according to the method disclosed in EP-219117 and JP-63 190 883, but operating in such conditions as to promote esterification instead of lactonization. For example, the radicalic addition of the hydrohalogen acid is followed by the reaction with alcohols in the presence of acids. The alcohols themselves can be used as reaction solvents.

The reaction of compounds (II) with 2,5-dimethylphenol is carried out preferably in the presence of acid-binding bases such as alkali or alkaline-earth metal carbonates, bicarbonates or hydroxides.

The reaction is carried out at a temperature ranging from 100° to 130° C., for a time from 1 to 3 hours.

The resulting gemfibrozil methyl ester is then hydrolysed with conventional methods, for example treating a methanol solution thereof with aqueous sodium hydroxide. The neutralization of the sodium salt with strong acids yields the desired compound.

The following example further illustrates the process of the invention.

EXAMPLE

A mixture of 30 kg of methyl 2,2-dimethyl-5-bromopentanoate, 50 kg of potassium carbonate, 40 kg 2,5-dimethylphenol and 3 kg of tetrabutyl ammonium bromide is heated to a temperature of 105°–115° C.

After that, a further 54 kg of methyl 2,2-dimethyl-5-bromopentanoate are added at such a rate as to keep temperature within the above indicated range. When the addition is over, temperature is maintained to 105°–115° C. for 3 hours. After cooling to 50°–70° C., 75 l of methanol are added, the mixture is cooled to 18°–20° C. and kept at this temperature for one hour, then filtered.

The mother liquors (methanol solution) are treated with 50 l of a 30% sodium hydroxide aqueous solution at the reflux temperature for 3 hours (pH>12,5). After distilling methanol, 325 l of water are added and the mixture is cooled to 25°–30° C. Gemfibrozil sodium salt precipitates (76 kg after recrystallization).

Acid gemfibrozil (69 kg) is recovered by treatment of the sodium salt with hydrochloric acid in acetone, m.p. 58°–61° C.

Potentiometric titre: 99.0–101.0% on the anhydrous base.

Purity (HPLC)>99.5%; column: HYPERSIL OVS C18, 250×4.6 mm, 5 micron; detector: UV 276 nm; eluent: AcOH 10 ml, MeOH 750 ml, to 1000 with water.

We claim:

1. A process for the preparation of 2,2-dimethyl-5-(2,5-xylyloxy) -valeric acid, which process comprises the reaction of 2,5-dimethylphenol with a compound of formula (II):

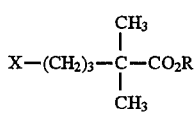

wherein R is an alkyl, aryl, arylalkyl group and X is a halogen atom, and the subsequent hydrolysis to compound (I), characterized in that the reaction of compound (II) with 2,5-dimethylphenol is carried out in the absence of solvents and in the presence of an ammonium or phosphonium quaternary salt.

2. A process according to claim 1, wherein in the compound of formula (II), X is bromine and R is ethyl or methyl.

3. A process according to claim 1, wherein the reaction of compound (II) with 2,5-dimethylphenol is carried out in the presence of alkali or alkaline-earth metal hydroxides, carbonates or bicarbonates.

4. A process according to claim 1, in which process the ammonium quaternary salt is tetrabutyl ammonium bromide.

* * * * *